United States Patent [19]
Syed

[11] Patent Number: 4,732,039
[45] Date of Patent: Mar. 22, 1988

[54] ACOUSTIC IMPEDANCE MEASUREMENT
[75] Inventor: Asif A. Syed, Loveland, Ohio
[73] Assignee: General Electric Company, Cincinnati, Ohio
[21] Appl. No.: 813,358
[22] Filed: Dec. 26, 1985
[51] Int. Cl.$^4$ ............................................. G01N 29/04
[52] U.S. Cl. ......................................... 73/589; 73/588
[58] Field of Search ........................... 73/589, 588, 591
[56] References Cited

U.S. PATENT DOCUMENTS

| | | | |
|---|---|---|---|
| 4,305,295 | 12/1981 | Andersson et al. | 73/589 |
| 4,397,187 | 8/1983 | Stribling | 73/589 |
| 4,537,630 | 8/1985 | Syed | 73/589 |

OTHER PUBLICATIONS

Article: "Error Analysis of Spectral Estimates with Application to the Measurement of Acoustic Parameters Using Random Sound Fields in Ducts", by A. F. Seybert and Benjamin Soenarko, J. Acoust. So. Am., vol. 69, No. 4, Apr., 1981, pp. 1190–1199.

Primary Examiner—Stewart J. Levy
Assistant Examiner—Louis M. Arana
Attorney, Agent, or Firm—Derek P. Lawrence

[57] ABSTRACT

A flexible U-shaped channel is abutted against a surface to be measured, thereby forming an acoustic duct, with the surface forming one wall of the duct. An acoustic source injects sound waves into the duct traveling parallel with the surface in order to establish a standing acoustic wave. Measurements of acoustic pressure at several points allows one to compute $k_y$, the acoustic wave number normal to the surface, and from $k_y$ to compute the acoustic impedance of the surface.

4 Claims, 4 Drawing Figures

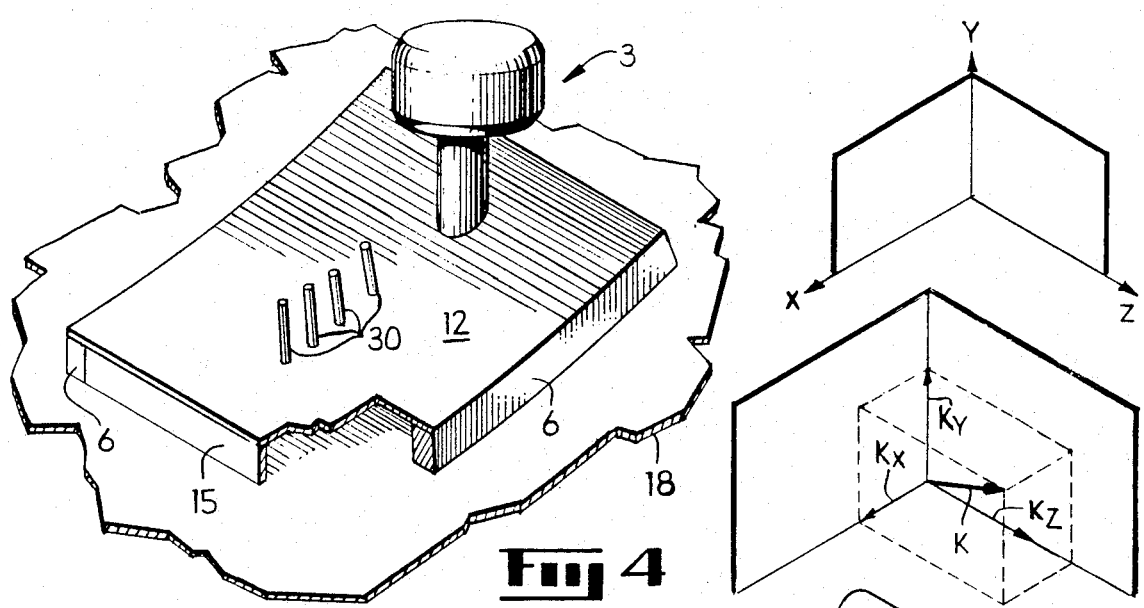
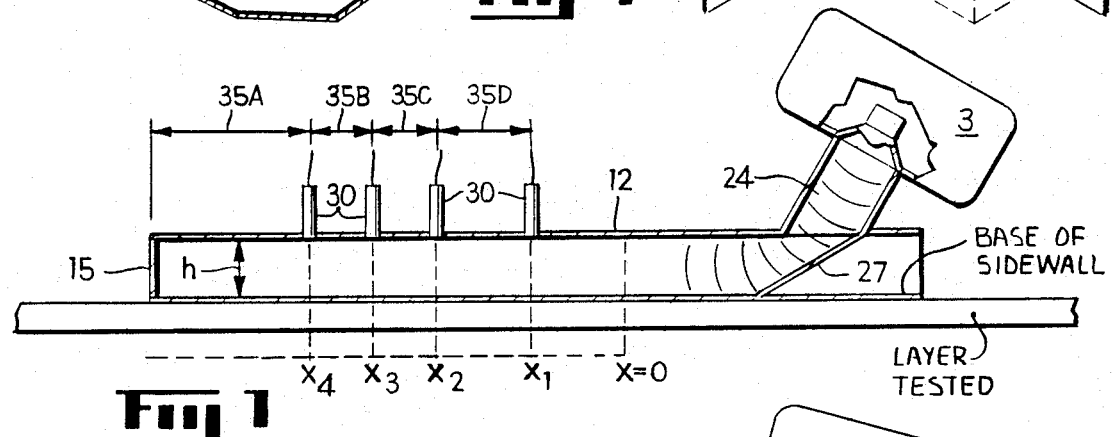
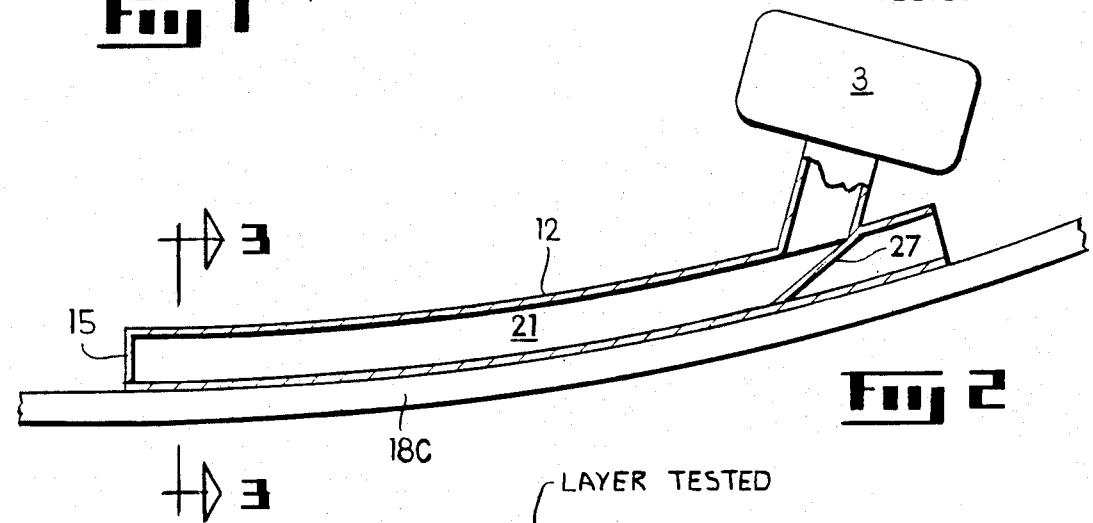
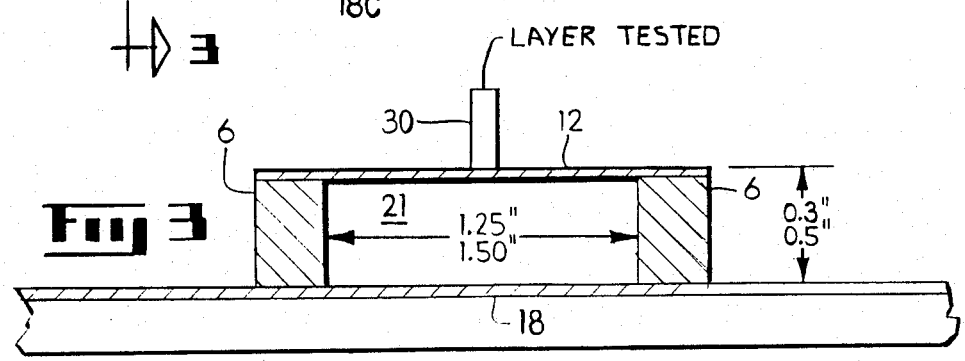

ACOUSTIC IMPEDANCE MEASUREMENT

The present invention relates to the measurement of the acoustic impedance of a material, and, more specifically, to the nondestructive measurement of the acoustic impedance of a material forming a curved surface.

BACKGROUND OF THE INVENTION

It is frequently desirable to measure the acoustic impedance of a material. The acoustic impedance gives information as to how much of an incoming sound wave is reflected and how much is absorbed. Thus, the acoustic impedance gives an indication of the sound-absorbing properties of the material.

Further, measurement of the acoustic impedance can give an indirect indication as to the structural properties of the material. For example, if the material includes a honeycomb laminated to a smooth outer sheet, a different acoustic impedance will be measured if the bonds between the honeycomb and the sheet are properly made as compared with the case of improperly formed bonds.

The measurement of acoustic impedance frequently requires that a slug of the material in question be cut from the material and inserted into what is called an acoustic impedance tube. Such cutting of course damages the material, thus perhaps rendering the cut region unusable. Therefore, this measurement procedure allows one to only make assumptions about the acoustic impedance of materials which have been manufactured under conditions similar to those of the cut material. One such material can be material in regions adjacent to the cut material. Another such material can be contained in an article manufactured in the same production batch as the cut material.

OBJECTS OF THE INVENTION

It is an object of the present invention to provide new and improved acoustic impedance measurement.

It is a further object of the present invention to provide nondestructive acoustic impedance measurement.

It is a further object of the present invention to provide direct acoustic impedance measurement of the actual regions of interest of an article, without damaging those regions.

It is a further object of the present invention to provide nondestructive acoustic impedance measurement of curved surfaces.

BRIEF DESCRIPTION OF THE DRAWING

FIG. 1 is a cross-sectional view of one form of the present invention.

FIG. 2 is a cross-sectional view of one form of the present invention, applied to a curved surface 18C.

FIG. 3 is a cross-sectional view of the invention in FIG. 2, taken along the lines 3—3.

FIG. 4 shows a perspective view of the invention of FIG. 2.

SUMMARY OF THE INVENTION

In one form of the present invention, a U-shaped channel is abutted against a surface to be measured, thereby forming an acoustic duct, with the surface forming one wall of the duct. An acoustic source injects sound waves into the duct traveling parallel with the surface in order to establish a standing acoustic wave. Measurements of acoustic pressure at several points allows one to compute $k_y$, the acoustic wave number normal to the surface, and from $k_y$ to compute the acoustic impedance of the surface.

DETAILED DESCRIPTION OF THE INVENTION

The present inventor has been awarded U.S. Pat. No. 4,537,630, issued Aug. 27, 1985, based on U.S. application Ser. No. 499,641, filed May 31, 1983. This patent concerns nondestructive acoustic impedance measurement, and is hereby incorporated by reference.

FIGS. 1–4 illustrate side, end, and perspective views of one form of the present invention respectively. In those Figures, 3 represents an acoustic speaker such as Model No. Altec 908-8B available from Altec Lansing, located in Anaheim, Calif. Side walls 6 in FIG. 3 are flexible, but acoustically hard, meaning that they reflect virtually all of the sound originating from speaker 3. Side walls 6 can be a hard rubber of duromoter 50 to 100, available from suppliers of gasket materials. Top wall 12 and end walls 15 are thin (preferably 18 gage), flexible sheet metal. These walls are likewise acoustically hard. As shown in FIG. 3, top wall 12 and side walls 6 cooperate with the surface of the material 18 to be tested to form a rectangular acoustic duct 21. The speaker 3 transmits sound waves 24 in FIG. 1 to a reflector 27 which reflects the sound waves along the surface 18. Over the frequency range of interest, the sound field consists of a single acoustic mode propagating parallel with the surface 18. The sound reflects from the end wall 15 to form a standing wave pattern (not shown). Pressure transducers 30, such as Model No. 8506A-2D, available from Endevco, located in San Juan Capistrano, Calif., measure acoustic pressure. From the pressure measurements the acoustic impedance of the surface 18 can be deduced as follows.

The standing wave established inside the duct can be expressed by the following equation $$p(t,x) = [A_o \exp(-ik_x x) + B_o \exp(ik_x x)] \exp(i\omega t)$$

The three acoustic wave numbers $k_x$, $k_y$, and $k_z$ illustrated in FIG. 4 are described by the following equation $$k^2 = k_x^2 + k_y^2 + k_z^2$$

wherein k is the acoustic wave Number (2 pi f/c) and wherein f is the frequency and c is the speed of sound within the duct. $K_z$ is zero over the range of frequencies of interest because of the selection of the width of the rectangular passage (i.e., higher order modes are cut off).

Thus, $k^2 = k_x^2 + k_y^2$.

It can be shown that the impedance of the surface 18 is given by the following equation $$Z(f) = i (k/k_y) COT(k_y h)$$

wherein h is the height of the duct 21.

See, for example, I. Malecki, Physical Foundations of Technical Acoustics, Permagon Press 1969, Library of Congress Catalog Card. No. 64-17267, pgs. 435–442. An example illustrating the procedure just described will now be given.

EXAMPLE

Consider the acoustic signals sensed, in FIG. 1, at locations $x_1$, $x_2$, $x_3$, and $x_4$ of the transducers relative to some reference location x=0. Let $\tilde{P}_1(f)$, $\tilde{P}_2(f)$, $\tilde{P}_3(f)$ and $P_4(f)$ be the values of the complex acoustic pressures measured by the transducers at frequency f. We can write the following set of equations:

$$A_o \exp(-ik_x x_1) + B_o \exp(ik_x x_1) = \tilde{P}_1(f)$$

$$A_o \exp(-ik_x x_2) + B_o \exp(ik_x x_2) = \tilde{P}_2(f)$$

$$A_o \exp(-ik_x x_3) + B_o \exp(ik_x x_3) = \tilde{P}_3(f)$$

$$A_o \exp(-ik_x x_4) + B_o \exp(ik_x x_4) = \tilde{P}_4(f)$$

There are three unknown quantities $A_o$, $B_o$, and $k_x$. We need a minimum of three equations to solve for these unknown quantities. The fourth equation represents a redundant measurement. The above equations can be solved for $A_o$, $B_o$, and $K_x$. $k_y$ can then be calculated from known values of k and $k_x$. Once $k_y$ is computed, the impedance Z(f) can readily be computed by the relationship $$Z(f) = i(k/k_y) \cot(k_y h)$$

The frequency range of the impendance measurement system is expected to be from 500 Hz to 10,000 Hz. The separation between adjacent transducers is expected to be between 0.25" and 1.5".

The preceding discussion and example have concerned measurement performed on a flat surface. However, frequently, the surface to be measured is not flat, but curved. The flexibility of the top wall 12 and side walls 6 accommodate the curvature by flexing to allow a continuous, acoustically tight fit between the side walls 6 and the surface 18. If the radius of curvature is large compared to the height h of the rectangular duct formed by the measurement system, then method described above for flat surfaces is also accurate for curved surfaces.

In the computation of impedance as described above, it has been assumed that the acoustically absorptive surface is locally reacting. This implies that inside the material being measured there is no transmission of sound in the x and z directions (i.e., no transmission parallel to the surface). In practice this condition is not generally met. Also, there is likely to be some leakage of sound due to imperfect seal between the flexible side walls 6 and the treatment surface 18. For the above reasons, a correction factor must be derived. The correction factor is defined by the following equation.

$$C(f) = Z(f)_N / Z(f)_a$$

The numerator, $z(f)_N$ is the normal acoustic impedance measured as known in the art by cutting out a slug of a reference material, which is similar in construction to the surface material 18 or 18c and inserting the slug into a measurement tube. One such measurement is described in the patent identified above.

The denominator, $z(f)_a$, is the "apparent" acoustical impedance as measured as described in the example above, but measured prior to cutting out the slug of the sample material for impendance tube measurement.

The correction factor gives a ratio indicating the degree of agreement between the actual acoustic impedance (measured destructively from the reference material in the impedance tube) and the apparent impedance (measured nondestructively from the sample material by the apparatus shown in FIG. 2 and by applying the equations above.)

Once the correction factor is ascertained for a given treatment design, measurements of other sample surfaces having shapes of the same design are taken, and an apparent impedance $Z(f)_a$ is computed as in the Example. Multiplication by the correction factor C(f) gives a good approximation, $Z(f)_{Naprx}$ of the actual impedance $Z(f)_N$ which would be measured destructively in an impedance tube. That is, $$Z(f)_{Naprx} = C(f) Z(f)_a$$

The inventor points out that the impedance is, of course, frequency-specific, as indicated by the notation Z(f). The correction factor is similarly frequency-specific. Thus, in actual use, many correction factors would be computed for a given surface 18C in FIG. 2, in order to compute the impedances for the frequencies of interest.

An invention has been described in which an "apparent" acoustic impedance of a reference material having a curved surface is measured using a procedure described above. Then, the acoustic impedance of the reference material is measured destructively, as known in the art, perhaps by using an impedance tube. A ratio of the apparent and actual impedances is taken, giving a correction factor.

Following derivation of the correction factor, the apparent impedance is measured on a sample material having the same design and construction as that of the reference. The apparent impedance is corrected by the correction factor in order to provide an estimate of actual normal acoustic impedance, $Z(f)_{Naprx}$, of the sample materials.

Numerous substitutions and modifications can be undertaken without modifying the true spirit and scope of the invention.

What is desired to be covered by Letters Patent is the invention as defined in the following claims:

1. Apparatus for measuring the acoustic impedance of a curved material, comprising:
   (a) a flexible, generally U-shaped channel having at least one acoustically hard wall for definining an end thereof, for abutting against the material and for forming an acoustic waveguide with the material, said waveguide having a generally rectangular cross section;
   (b) a plurality of acoustic transducers for measuring pressure at a respective plurality of locations within the waveguide; and
   (c) speaker means for injecting planar sound waves into the waveguide having a direction of propagation generally parallel with the surface of the material to establish a standing wave in said waveguide.

2. A method of estimating the normal acoustic impedance of sample material, comprising the following steps:
   (a) abutting a flexible channel to the surface of a reference material to thereby form an acoustic waveguide;
   (b) generating a standing wave within the waveguide by propagating sound waves in a direction generally parallel with the surface of the reference material;
   (c) measuring acoustic pressure at a plurality of locations;
   (d) computing the acoustic wave number, $k_y$, which is perpendicular to the surface of the material;

(e) computing an apparent impedance from the following equation:

$$Z(f)_a = i(k/k_y) \, COT \, (k_y h)$$

wherein $Z(f)a$ designates apparent acoustic impedance, i indicates that the expression following it is an imaginary number (that is, $i^2 = -1$), k is the acoustic wave number, Ky is the acoustic wave number perpendicular to the surface of the material, and h is the height of the waveguide;

(f) computing a correction factor, C(f), based on the known acoustic impedance of the material and the apparent acoustic impedance;

(g) repeating steps (a)-(e) upon the sample material in order to derive a second apparent impedance; and (h) estimating the normal acoustic impedance of the material based on the second apparent impedance and the correction factor.

3. An apparatus according to claim 1 in which the U-shaped channel has a substantially constant cross-section along the length of the channel.

4. A method according to claim 2 in which the standing wave is of a type which can be described by the following expression:

$$P(f) = A \exp(-i \, k_x x) + B \exp(i k_x x)$$

wherein P refers to pressure, f refers to frequency, i is the imaginary index, defined such that $i^2 = -i$, A and B are constants representing wave amplitude, $k_x$ is the acoustic wave number parallel with the surface of the material, and x represents position in the waveguide.

* * * * *